United States Patent [19]

Koga et al.

[11] Patent Number: 5,214,199
[45] Date of Patent: May 25, 1993

[54] PROCESS FOR PREPARING MALONIC MONOESTER

[75] Inventors: Teruyoshi Koga, Takasago; Noboru Ueyama; Kenji Inoue, both of Kakogawa; Satomi Takahashi, Kobe, all of Japan

[73] Assignee: Kanegafuchi Chemical Industries Co., Ltd., Osaka, Japan

[21] Appl. No.: 755,496

[22] Filed: Aug. 30, 1991

[30] Foreign Application Priority Data

Sep. 1, 1990 [JP] Japan .................. 2-231335

[51] Int. Cl.$^5$ ............................................. C07C 67/08
[52] U.S. Cl. ..................................... 560/204; 560/193; 562/590
[58] Field of Search .............................. 560/193, 204

[56] References Cited

U.S. PATENT DOCUMENTS

| 4,360,691 | 11/1982 | Perrin ................................. 560/131 |
| 4,399,300 | 8/1983 | Prange et al. ......................... 560/204 |
| 4,827,022 | 5/1989 | Makowka et al. .................... 560/204 |
| 4,904,814 | 2/1990 | Frei et al. ............................ 560/204 |

OTHER PUBLICATIONS

*Beilsteins Handbuchder Organischen Chemie,* 4th Edition, vol. 2, 1976, p. 1885.
*Beilsteins Handbuchder Organischen Chemie,* 4th Edition, vol. 2, 1961, pp. 1620–1621.
*Methodender Organischen Chemie,* vol. E5, 1985, pp. 671–672.

*Primary Examiner*—José G. Dees
*Assistant Examiner*—Vera C. Clarke
*Attorney, Agent, or Firm*—Wegner, Cantor, Mueller & Player

[57] ABSTRACT

A malonic monoester is prepared in a good yield by a single step reaction by reacting malonic acid with an alcohol in the presence of a base and an activator of malonic acid selected from the group consisting of an acyl halide or halocarbonate and an acid anhydride or dicarbonate.

8 Claims, No Drawings

PROCESS FOR PREPARING MALONIC MONOESTER

BACKGROUND OF THE INVENTION

1. Field of the Invention

The present invention relates to a process for preparing a malonic monoester which is useful as an intermediate in the production of medicines or agricultural chemicals.

2. Description of the Related Art

Hitherto, a malonic monoester has been prepared by (1) partially hydrolyzing a malonate diester which is prepared from malonic acid (see Org. Synthesis Coll., 4, 417 (1963)), (2) partially hydrolyzing di-tert.-butyl malonate which is prepared from diethyl malonate (see Carbohydr. Res., 169, 171 (1987)), (3) partially hydrolyzing di-tert.-butyl malonate which is prepared from malonic acid (see Rec. Trav. Chim., 58, 1048 (1939)), or (4) reacting tert.-butylisocyanide with malonic acid and an alcohol (see J. Chem. Res., 119 (1977)).

All of these processes have drawbacks such as requirement of multistep reactions, low yields or the use of expensive reagents, and are not suitable as technical processes for the preparation of a malonic monoester.

SUMMARY OF THE INVENTION

An object of the present invention is to provide a novel process for preparing a malonic monoester from cheap starting materials in one step in a high yield.

According to the present invention, there is provided a process for preparing a malonic monoester comprising reacting malonic acid with an alcohol of the formula:

$$R_1-OH \qquad (I)$$

wherein $R_1$ is an alkyl group, an allyl group, an aryl group or an aralkyl group, in the presence of a base and an activator of malonic acid selected from the group consisting of an acyl halide or halocarbonate of the formula:

$$R_2-A-X \qquad (II)$$

wherein $R_2$ is an alkyl group or a substituted or unsubstituted aryl group, A is $-SO_2-$, $-CO-$ or $-OCO-$, and X is a chlorine atom or a bromine atom and an acid anhydride or dicarbonate of the formula:

$$R_2-A-O-E-R_3 \qquad (III)$$

wherein $R_2$ and A are the same as defined above, E is $-SO_2-$, $-CO-$ or $-COO-$, and $R_3$ is an alkyl group, an allyl group, an aryl group or an aralkyl group provided that $R_2$ and $R_3$ may be the same or different.

DESCRIPTION OF THE INVENTION

In the present invention, an alkyl group is intended to mean a straight or branched alkyl group having 1 to 20 carbon atoms, preferably 1 to 10 carbon atoms. An aryl group is intended to mean a substituted or unsubstituted aryl group having 6 to 15 carbon atoms, preferably 6 to 10 carbon atoms (e.g. a phenyl group, a tolyl group, a m-chlorophenyl group, a p-nitrophenyl group, etc.), and an aralkyl group is intended to mean 7 to 16 carbon atoms, preferably 7 to 11 carbon atoms. A substituent of an aryl group includes an alkyl group having 1 to 5 carbon atoms, an alkoxy group having 1 to 5 carbon atoms, a hydroxyl group, a halogen atom and a nitro group.

An amount of the alcohol (I) is from 1 to 50 moles, preferably 2 to 20 moles per one mole of malonic acid.

Examples of the base is amines (e.g. triethylamine, trimethylamine, diisopropylethylamine, N-methyl piperidine, etc.), alkali metal carbonates, alkali metal alkoxides (e.g. sodium ethoxide, sodium methoxide, potassium tert.-butoxide, sodium carbonate, potassium carbonate, etc.), alkali metal hydrides, etc. In view of yield or handleability, the amines, in particular pyridine which may be substituted with an alkyl group having 1 to 5 carbon atoms, an amino group having 1 to 10 carbon atoms or a hydroxy group are preferred. An amount of the base is from 1 to 3 moles, preferably 2 to 2.6 moles per one mole of malonic acid, though a suitable amount of the base varies with a kind of the base and also a kind of the activator.

Among the activators (II) and (III), the acyl chloride of a carboxylic acid or sulfonic acid and the acid anhydride are preferred. In particular, acetic anhydride, methanesulfonyl chloride and acetyl chloride are preferred.

An amount of the activator is from 1 to 2 moles, preferably from 1 to 1.3 moles per one mole of malonic acid, though a suitable amount of the activator varies with a kind of the activator and also a kind of the base.

The reaction may be carried out in a solvent. Preferred examples of the solvent are ethers (e.g. tetrahydrofuran, dioxane, dimethoxyethane, etc.), aromatic hydrocarbons (e.g. benzene, toluene, etc.), halogenated hydrocarbons (e.g. methylene chloride, chloroform, trichloroethane, etc.), esters (e.g. ethyl acetate, methyl acetate, etc.), and an alcohol to be used for esterification. In view of the yield and handleability, the ether and the ester, in particular, tetrahydrofuran and ethyl acetate are preferred.

A reaction temperature is from $-20°$ to $+50°$ C., preferably from $-10°$ to $+50°$ C., more preferably from $-10$ to $30°$ C.

A reaction time depends on other reaction conditions such as the reaction temperature and is usually from 1 to 48 hours, preferably from 2 to 24 hours. In general, the acid anhydride requires a longer reaction time than the acyl halide.

The malonic monoester is recovered from a reaction mixture by a conventional method such as distillation, extraction, crystallization and the like.

PREFERRED EMBODIMENTS OF THE INVENTION

The present invention will be illustrated by following Examples.

Example 1

Synthesis of mono-tert.-butyl malonate

To a solution of malonic acid (5.2 g, 50 mmol) in tetrahydrofuran (40 ml), pyridine (9.1 g, 115 mmol) and tert.-butanol (10 ml, 106 mmol) were added and stirred, followed by cooling to 0° C. To the mixture, methanesulfonyl chloride (6.59 g, 57.5 mmol) was added over 20 minutes and stirred for one hour. Then, methylene chloride (30 ml) and water (10 ml) were added, and pH of the mixture was adjusted to 10 to 11 with a 30% aqueous solution of sodium hydroxide. The mixture was separated and an aqueous layer was washed with methylene chloride (10 ml) three times. After adjusting pH of the aqueous layer to 2.5 with 6N hydrochloric acid, the aqueous layer was extracted with methylene chloride (30 ml) four times. The combined organic layer was dried over sodium sulfate and concentrated to obtain the substantially pure entitled compound (5.64 g). Yield, 70%.

$^1$H-NMR (CDCl$_3$): δ=1.45 (s, 9H), 3.33 (s, 2H), 9.97 (brs. 1H).

IR (neat): 3000, 1730, 1160 cm$^{-1}$.

Example 2

Synthesis of mono-tert.-butyl malonate

To a solution of malonic acid (5.2 g, 50 mmol) in tetrahydrofuran (40 ml), pyridine (9.1 g, 115 mmol) and tert.-butanol (10 ml, 106 mmol) were added and stirred, followed by cooling to 0° C. To the mixture, methanesulfonyl chloride (6.59 g, 57.5 mmol) was added over 20 minutes and stirred for one hour. A precipitated salt was filtered off. To a filtrate, ethyl acetate (30 ml) and water (100 ml) were added, and pH of the mixture was adjusted to 8 to 9 with a 20% aqueous solution of sodium hydroxide. The mixture was separated and an aqueous layer was washed with methylene chloride (50 ml) three times. After adjusting pH of the aqueous layer to 2.5 with conc. hydrochloric acid, the aqueous layer was extracted with methylene chloride (50 ml) eight times. The combined organic layer was dried over sodium sulfate and concentrated to obtain the substantially pure entitled compound (5.71 g). Yield, 71%.

The results of $^1$H-NMR and IR were the same as those in Example 1.

Example 3

Synthesis of mono-tert.-butyl malonate

To a solution of malonic acid (5.2 g, 50 mmol) in tetrahydrofuran (40 ml), pyridine (9.49 g, 62 mmol) and tert.-butanol (10 ml, 106 mmol) were added and stirred, followed by cooling to 0° C. To the mixture, acetic anhydride (6.13 g, 60 mmol) was added over 20 minutes and stirred for 10 minutes at 0° C. and then 5 hours at room temperature. After concentrating the reaction mixture under reduced pressure, methylene chloride (30 ml) and water (10 ml) were added, and pH of the mixture was adjusted to 10 to 11 with a 30% aqueous solution of sodium hydroxide followed by stirring for one hour at room temperature. The mixture was separated and an aqueous layer was washed with methylene chloride (10 ml) three times. After adjusting pH of the aqueous layer to 2.5 with 6N hydrochloric acid, the aqueous layer was extracted with methylene chloride (30 ml) four times. The combined organic layer was dried over sodium sulfate and concentrated to obtain crude mono-tert.-butyl malonate, which was concentrated under reduced pressure in order to remove acetic acid to obtain the substantially pure entitled compound (5.37 g). Yield, 67%.

The results of $^1$H-NMR and IR were the same as those in Example 1.

Example 4

Synthesis of mono-tert.-butyl malonate

In the same manner as in Example 3 but using di-tert.-butyl dicarbonate (13.1 g, 60 mmol) in place of acetic anhydride, the reaction was carried out to obtain the substantially pure entitled compound (3.88 g). Yield, 48%.

The results of $^1$H-NMR and IR were the same as those in Example 1.

Example 5

Synthesis of monoethyl malonate

To a solution of malonic acid (5.2 g, 50 mmol) in tetrahydrofuran (40 ml), pyridine (9.1 g, 115 mmol) and ethanol (5.9 ml, 102 mmol) were added and stirred, followed by cooling to 0° C. To the mixture, methanesulfonyl chloride (6.59 g, 57.5 mmol) was added over 20 minutes and stirred for one hour. Then, methylene chloride (30 ml) and water (10 ml) were added. pH of the mixture was adjusted to 10 to 11 with a 30% aqueous solution of sodium hydroxide. The mixture was separated and an aqueous layer was washed with methylene chloride (10 ml) three times. After adjusting pH of the aqueous layer to 2.5 with 6N hydrochloric acid, the aqueous layer was extracted with methylene chloride (30 ml) four times. The combined organic layer was dried over sodium sulfate and concentrated to obtain the substantially pure entitled compound (2.38 g). Yield, 35%.

$^1$H-NMR (CDCl$_3$): δ=1.3 (t, 3H), 3.43 (s, 2H), 4.29 (q, 2H), 9.32 (brs., 1H).

Example 6

Synthesis of monoisopropyl malonate

To a solution of malonic acid (5.2 g, 50 mmol) in tetrahydrofuran (40 ml), pyridine (9.1 g, 115 mmol) and isopropanol (7.65 ml, 99 mmol) were added and stirred, followed by cooling to 0° C. To the mixture, methanesulfonyl chloride (6.59 g, 57.5 mmol) was added over 20 minutes and stirred for one hour. Then, methylene chloride (30 ml) and water (10 ml) were added, and pH of the mixture was adjusted to 10 to 11 with a 30% aqueous solution of sodium hydroxide. The mixture was separated and an aqueous layer was washed with methylene chloride (10 ml) three times. After adjusting pH of the aqueous layer to 2.5 with 6N hydrochloric acid, the aqueous layer was extracted with methylene chloride (30 ml) four times. The combined organic layer was dried over sodium sulfate and concentrated to obtain the substantially pure entitled compound (4.71 g). Yield, 65%.

$^1$H-NMR (CDCl$_3$): δ=1.3 (d, 6H), 3.37 (s, 2H), 5.07 (m, 1H), 8.78 (brs., 1H).

Example 7

Synthesis of monobenzyl malonate

To a solution of malonic acid (5.2 g, 50 mmol) in tetrahydrofuran (40 ml), pyridine (9.1 g, 115 mmol) and benzyl alcohol (10.35 ml, 100 mmol) were added and stirred, followed by cooling to 0° C. To the mixture, methanesulfonyl chloride (6.59 g, 57.5 mmol) was added over 20 minutes and stirred for one hour. Then, methylene chloride (30 ml) and water (10 ml) were added, and pH of the mixture was adjusted to 10 to 11 with a 30% aqueous solution of sodium hydroxide. The mixture was separated and an aqueous layer was washed with methylene chloride (10 ml) three times. After adjusting pH of the aqueous layer to 2.5 with 6N hydrochloric acid, the aqueous layer was extracted with methylene chloride (30 ml) four times. The combined organic layer was dried over sodium sulfate and concentrated to obtain the substantially pure entitled compound (4.80 g). Yield, 49%.

$^1$H-NMR (CDCl$_3$): δ=3.44 (s, 2H), 5.17 (s, 2H), 7.33 (s, 5H), 8.27 (brs., 1H).

What is claimed is:

1. A process for preparing a malonic monoester comprising reacting malonic acid with an alcohol of the formula:

$$R_1\text{—OH} \qquad (I)$$

wherein $R_1$ is an alkyl group, an allyl group, an aryl group or an aralkyl group, in the presence of a base and an activator of malonic acid selected from the group consisting of an acyl halide or halocarbonate of the formula:

$$R_2\text{—A—X} \qquad (II)$$

wherein $R_2$ is an alkyl group, an aryl group, or an aryl group having a substituent selected from the group consisting of C$_{1-5}$ alkyl, C$_{1-5}$ alkoxy, hydroxy, halogen, and nitro, A is —SO$_2$—, —CO— or —OCO—, and X is a chlorine atom or a bromine atom and an acid anhydride or dicarbonate of the formula:

$$R_2\text{—A—O—E—R}_3 \qquad (III)$$

wherein $R_2$ and A are the same as defined above, E is —SO$_2$—, —CO— or —COO—, and R$_3$ is an alkyl group, an allyl group, an aryl group or an aralkyl group provided that R$_2$ and R$_3$ may be the same or different;

wherein the amount of said alcohol is from 1 to 50 moles per one mole of malonic acid, the amount of said activator is at least one mole per one mole of malonic acid, and the temperature range of said reaction is from −20 C to 50 C.

2. The process according to claim 1, wherein said base is an amine.

3. The process according to claim 1, wherein said base is pyridine which may be substituted.

4. The process according to claim 1, wherein said acyl halide is methanesulfonyl chloride.

5. The process according to claim 1, wherein said acyl halide is acetyl chloride.

6. The process according to claim 1, wherein said acid anhydride is acetic anhydride.

7. The process according to claim 1, wherein said alcohol is tert.-butanol.

8. The process according to claim 1, wherein said dicarbonate is tert.-butyl dicarbonate.

* * * * *